United States Patent
Roberts

(10) Patent No.: US 6,301,359 B1
(45) Date of Patent: Oct. 9, 2001

(54) TELEPHONE HANDSET STERILIZER METHOD AND APPARATUS

(76) Inventor: Jon L. Roberts, 529 Clear Spring Rd., Great Falls, VA (US) 22066

( * ) Notice: Subject to any disclaimer, the term of this patent is extended or adjusted under 35 U.S.C. 154(b) by 0 days.

(21) Appl. No.: 09/228,263

(22) Filed: Jan. 11, 1999

(51) Int. Cl.[7] ................................................ H04M 1/00
(52) U.S. Cl. ................................ 379/452; 379/439
(58) Field of Search ................................ 379/452, 451, 379/439, 437

(56) References Cited

U.S. PATENT DOCUMENTS

| | | | |
|---|---|---|---|
| 3,954,407 | 5/1976 | Andary | 21/83 |
| 4,100,415 | 7/1978 | Blaisdell et al. | 250/455 |
| 4,772,795 | 9/1988 | Sakurai et al. | 250/455.1 |
| 4,806,770 | 2/1989 | Hylton et al. | 250/455.1 |
| 4,973,847 | 11/1990 | Lackey et al. | 250/455.1 |
| 5,008,933 | * 4/1991 | Kao et al. | 379/452 |
| 5,023,460 | 6/1991 | Foster, Jr. et al. | 250/455.1 |
| 5,126,572 | 6/1992 | Chu | 250/455.11 |
| 5,127,521 | 7/1992 | Bourque | 206/362.1 |
| 5,396,557 | * 3/1995 | Tonic | 379/452 |
| 5,487,877 | 1/1996 | Choi | 422/300 |
| 5,547,635 | 8/1996 | Duthie | 422/24 |

FOREIGN PATENT DOCUMENTS

531883 * 12/1957 (BE) ................................. 379/452

* cited by examiner

*Primary Examiner*—Jack Chiang
(74) *Attorney, Agent, or Firm*—Roberts Abokhair & Mardula LLC

(57) ABSTRACT

A telephone handset sterilization apparatus and method having ultraviolet sterilization of the mouthpiece and earpiece of a telephone handset. The invention has an ultraviolet source within the earpiece and mouthpiece cradles of a telephone handset cradle. The telephone handset engages a seal around the earpiece and mouthpiece which blocks UV illumination from a user and seals in ozone gas that is produced by UV source below 200 nm. The UV source illuminated the earpiece and mouthpiece of a telephone handset when the handset is in the on-hook position. When on-hook, the handset engages a switch which signals a timer/power circuit which provides a timed application of power to the UV source(s). The duty cycle of the UV source os timed for substantially complete sterilization of the telephone handset. Minute amounts of ozone gas surround the earpiece and mouthpiece of the telephone handset providing more complete sterilization. An alternate embodiment can be retrofit to existing telephones. An additional alternate embodiment has a cover that encloses the telephone handset and contains additional UV lamps for sterilizing the complete handset. The sterilizer switch turns the unit off when the telephone handset is lifted off hook or when the cover is opened.

35 Claims, 5 Drawing Sheets

TELEPHONE HANDSET STERILIZER METHOD AND APPARATUS

FIELD OF THE INVENTION

The present invention relates generally to sterilization devices. More particularly this invention relates to a device for sterilizing the handset of telephone including vertically mounted telephones, horizontally resting telephones, and domestic and public telephones using ultraviolet radiation.

BACKGROUND OF THE INVENTION

It has long been known that germs are spread by, among other things, hand to hand contact. Hence there's been much in the literature recently concerning the washing of hands in order to prevent the spreading of the common cold as well as other microbes. Recently, it has even been discovered that bacteria continue to live on writing implements there used by individuals. As such, writing implements can also carry microbes and therefore can be a vector for the spread of disease. Telephones are no less apt to be a vector for the spread of germs. In fact, this is even more the case since individuals breathe into telephones and deposit germs thereon. It is bad enough in one's own family environment, but the spread of germs from one stranger to another via telephone handsets of public telephones, or office telephones is equally a menace.

Many objects are sterilized. For example, hospitals use sterilization routinely for surgical instruments. Typically such sterilization occurs both chemically as well as through high-pressure high temperature steam sterilization. This results in generally sterile instruments for use in surgery. The difficulty, of course, is that such devices are expensive, cumbersome, and are therefore not practical for the widespread sterilization of more common devices.

The spread of germs via bathroom articles has been the subject of invention. For example, U.S. Pat. No. 3,954,407 to Andary et al., U.S. Pat. No. 4,088,445 to Ellis, U.S. Pat. No. 4,88,4072 Ritter, U.S. Pat. No. 4,772,795 to Sakurai et al. U.S. Pat. No. 4,803,364 to Ritter and U.S. Pat. No. 4,806,770 to Hylton et al. all disclose methods of sterizing toothbrucshes and dental articles using ultraviolet lamps.

Similarly U.S. Pat. No. 4,906,851 to Beasley et al., U.S. Pat. No. 4,973,847 to Lackey et al., U.S. Pat. No. 5,023,460 to Foster, Jr. et al., U.S. Pat. No. 5,126,572 to Chu, and U.S. Pat. No. 5,127,521 to Bourgue, all disclsoe ultraviolet based toothbrush sterilizers, while U.S. Pat. No. 5,487,877 to Choi, and U.S. Pat. No. 5,547,635 to Duthei, Jr. disclose general sterilization methods and apparatus wherein microorganisms are exposed to ultraviolet light. Thus it can be seen that much work has been done with respect to the sterilization of bathroom articles. However no attention has been paid to the sterilization of other common implements, specifically telephones which can clearly carry disease generating microorganisms.

It would therefore be desirable to have a convenient, readily available method and apparatus for sterilizing telephones, specifically the telephone handset, thereby preventing the transmission of object-borne disease spreading microorganisms.

SUMMARY OF THE INVENTION

It is therefore an object to the present invention to sterilize telephones, specifically the telephone handset.

It is a further object of present invention to provide a telephone handset sterilization apparatus that can be commonly available and easy to use.

It is a further object of the present invention to provide a sterilization apparatus using ultraviolet radiation as a means of sterilization of the telephone handset.

It is a further object of present invention to combine ultraviolet sterilization and ozone sterilization together to more completely sterilize telephone handsets.

It is a further object of the present invention to provide a sterilization device for sterilizing telephone handsets safely and without exposing a user to ultraviolet sterilization radiation.

It is a further object of a present invention to provide a telephone handset sterilizer that operates on normal wall current or battery power.

It is yet another objective of the present invention to provide a telephone handset sterilizer apparatus that operates automatically when the telephone is on hook and that is off when the telephone is off hook so as to minimize the exposure of the user to ultraviolet radiation.

It is a further object of the present invention to provide the telephone handset sterilization via sterilization units built into new telephones and by retrofitting existing telephones with a removably attached module that sterilizes telephone handsets.

These and other objects of the present invention will become apparent to those skilled in the art by review of the specification that follows.

The present invention is a telephone sterilizer that sterilizes the handset of telephones. The present invention comprises generally an ultraviolet light source particularly in approximately the 200 to 300 nm wavelength range. This UV range is known for its germicidal and sterilization effects achieved by direct radiation. It is also-known that ultraviolet radiation below 200 nm can produce small quantities of ozone from oxygen in the atmosphere. Ozone, in sufficient concentrations is known to have significant germicidal and sterilization effects. Further, ozone, as a gas, is able to reach certain places and crevices in telephone handsets, for example holes or apertures in front of the handset microphone or apertures in front of the handset speaker where ultraviolet radiation might not reach. Thus the present invention uses both UV light sources that produce ozone (i.e. 200 nm and below) and those UV sources that do not (i.e. above 200 nm).

The ultraviolet light source of the present invention is mounted within a handset cradle such that the ultraviolet radiation can shine directly upon and reflect onto the earpiece and the microphone portion of a telephone handset once the telephone handset is replaced in the handset cradle (i.e. the telephone is place back on-hook).

For purposes of this specification the following definitions apply:

Telephone handset cradle: the general structure on telephones in which a telephone handset rests when the telephone is on-hook.

Earpiece cradle: the portion of the telephone handset cradle in which the earpiece of the telephone handset (the part to which a user listens) rests when the telephone is on-hook.

Mouthpiece cradle: the portion of the telephone handset cradle in which the mouthpiece of the telephone handset (the part the user speaks into) rests when the telephone is on-hook.

The ultraviolet light source can be mounted in a number of configurations. For example, the ultraviolet lamp can be a ring type lamp at the base and around the perimeter of the earpiece and mouthpiece cradles respectively. Alternatively tubular ultraviolet lamps can be dispose in the portion of the telephone handset cradle to illuminate the earpiece and mouthpiece.

The wavelength range of the ultraviolet radiation of the preferred embodiment of the present invention also causes a small amount of ozone to be generated. This ozone is released into the telephone handset cradle and together with the ultraviolet radiation provides a more complete sterilization of the earpiece and mouthpiece portions of the telephone handsets. In an alternative embodiment, UV radiation which does not produce ozone (i.e. above 200 nm) is used for those areas that are too enclosed, do not have proper ventilation, or where regulations so dictate.

In an alternative embodiment the present invention also comprises a top or lid (a "telephone handset cradle cover") which is hingedly or removably attached to the sterilization telephone handset cradle. This telephone handset cradle cover prevents ultraviolet radiation from escaping the area in which sterilization occurs thereby protecting any users or those who pass by the sterilization apparatus. It also contains ultraviolet lamps so that when the lid is closed over the telephone handset, the entire handset is bathed in ultraviolet radiation and surrounded by ozone (if the appropriate UV source is present) to provide complete sterilization of not only the earpiece and microphone (mouthpiece) portion of the handset but of the handle and entire handset as well.

Integral to the telephone handset cradle and its telephone handset cradle cover, is an interlocking switch, preferably spring loaded, and which is biased in the "off" position. When the telephone is in the on-hook position, or when a telephone handset cradle cover is present, when the telephone handset cradle cover is placed over the telephone handset, the switch is engaged and the ultraviolet radiation light source is turned on. When the telephone is in the off-hook position, or when the handset cover is lifted to make a telephone call, the ultraviolet radiation is immediately turned off as soon as the telephone handset is lifted or the telephone handset cradle cover is removed.

A timer/power circuit for the ultraviolet light source is an integral part of present invention and delivers power to the UV light sources for a specified period of time. The timing circuit is activated as soon as the telephone is placed on-hook or the telephone handset cradle cover is replaced. The timer/power circuit allows the ultraviolet light sources to remain on for a predetermined amount of time. This time is consistent with substantially complete sterilization of the telephone handset (the "sterilization time"). When the appropriate sterilization time has expired, the ultraviolet light source is turned off thereby 1) saving power if the unit is battery powered, 2) prolonging the life of the ultraviolet light source(s), and 3) halting the generation of ozone within the telephone handset cradle. In the event that the telephone handset is lifted off-hook or the telephone handset cradle cover is lifted, the UV lamps are immediately turned off and the timer is reset. Upon replacing the handset on-hook, or upon closing of the telephone handset cradle cover, the sterilization time period begins again and the UV lamps are turned on.

The present invention is used for desk telephones, wall mounted telephones public (pay) telephones, and all manner of handsets requiring sterilization. The telephone handset cradle may also comprise either a screen or other porous and/or transparent material that can both support the telephone handset as well as allow the passage of ultraviolet light and ozone. Alternatively the present invention may comprises a quartz housing for the handset with UV lamps disposed below and around the quartz housing such that the ultraviolet light is allowed to pass through the quartz housing while still supporting the telephone handset. In those cases where a quartz supporting mechanism is used, sufficient gaps between the housing and quartz supporting mechanism are present to allow ozone gas to diffuse about the handset earpiece and mouthpiece as well as around the telephone handset in the embodiment where a telephone handset cradle cover is employed, thereby providing further sterilization.

A further part of the present invention is a seal made from rubber or silicone or some similar material such that when the telephone handset is place in the sterilization telephone cradle, a tight seal between the mouthpiece cradle and the mouthpiece and earpiece cradle and the earpiece is achieved. These seals shield users from UV light and keep any ozone generated in the immediate vicinity of the mouthpiece and earpiece respectively.

The present invention also comprises an indicator light whereby, when sterilization is proceeding, the indicator light is lit. When sterilization is not occurring, as in the case when the telephone handset is in the off-hook position, the handset cover is lifted, the sterilization lamp has burned out, and/or the sterilization time period has run, the indicator light is extinguished.

The present invention can operate both on normal household current found in homes, businesses, and buildings of all types as well as on battery power. Where battery power is used it is anticipated that rechargeable batteries will be present in the present invention such that sterilization can continue to take place for some period of time even during power failures. Alternatively, single use batteries are a perfectly appropriate source of energy to power the UV lamps of the current invention.

An alternate embodiment of the present invention comprises a sterilizing handset cradle that can be retrofitted to existing telephones (a "retrofit handset sterilizer"). This retrofit handset sterilizer has all of the components of the telephone sterilizer that is integral to a normal telephone but simply fits over the normal handset "cradle" that exists on most telephones. The only additional mechanism is an engaging member or means that will removably connect to the typical "on-hook" switch in the normal telephone cradle when the retrofit handset sterilizer is placed in the normal telephone cradle. Thus when the telephone handset is placed on-hook in the retrofit handset sterilizer, the on-hook switch of the normal telephone will be engaged as well. Thereafter, telephone handset sterilization will continue as described above.

BRIEF DESCRIPTION OF THE DRAWINGS

The present invention is now described by way of example with references to the accompanying drawings.

DETAILED DESCRIPTION OF THE INVENTION

Figure 1:
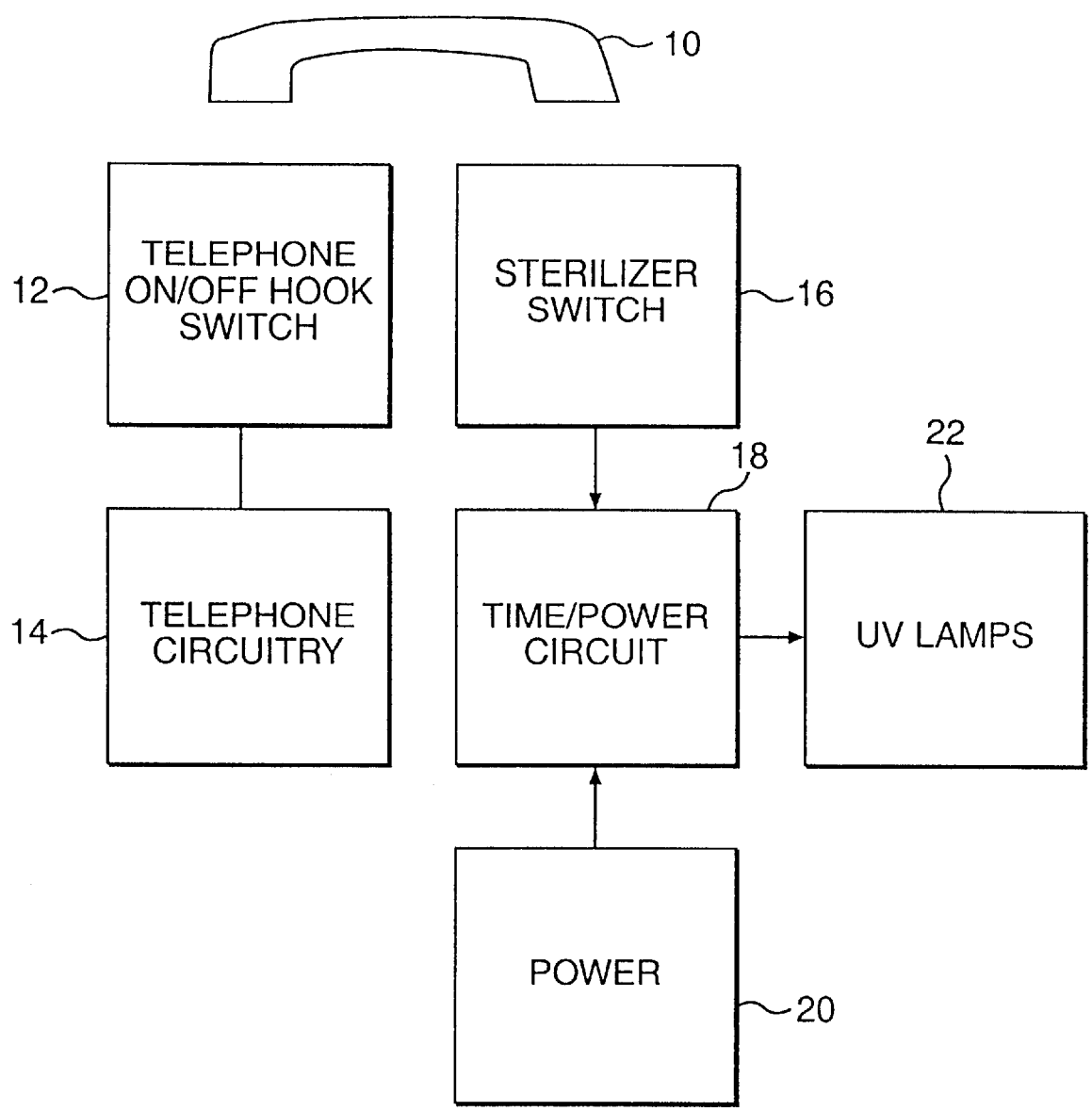
FIG. 1 illustrates a schematic of the present invention.

Referring to FIG. 1 a schematic of the present invention is illustrated. Telephone 10, when place in an on-hook condition, actuates both the normal telephone on/off hook switch 12 as well as the telephone handset sterilizer switch 16 which is spring loaded and normally biased in the "off" position. Whether on or off hook, the normal telephone circuitry 14 is not affected in any way.

When the telephone handset sterilizer switch 16 is actuated, the timer/power circuit is energized and power from the power source 20 is applied to the UV lamps and the timer/power circuit begins a preset timing cycle during which sterilization occurs.

The power 20 can be supplied by batteries, or power from normal household current, with some form of step-down transformer typically used to diminish the current flowing to the telephone.

Figure 2:
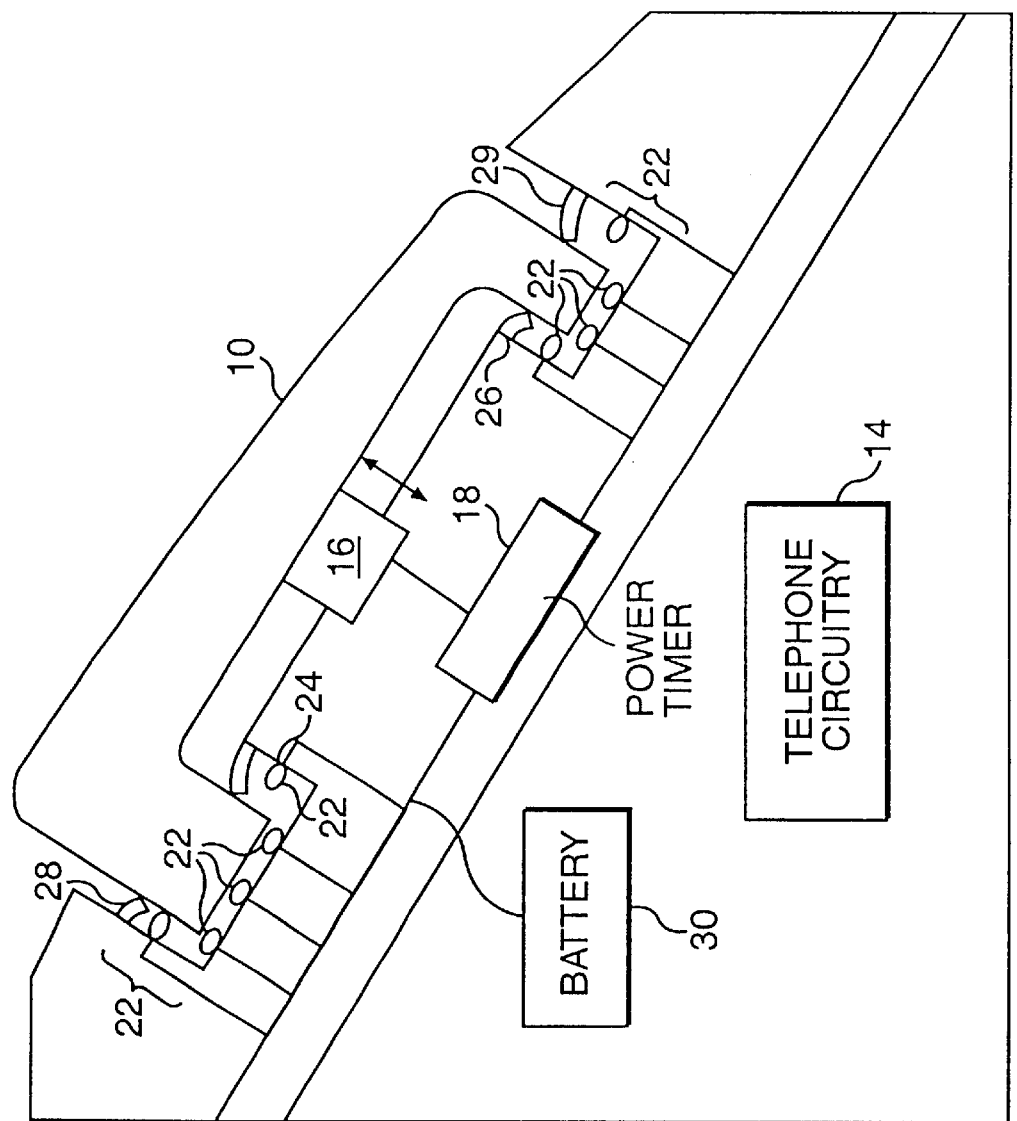
FIG. 2 illustrates the telephone handset sterilizer with a telephone handset in the on hook position.

Referring to FIG. 2 the telephone handset sterilizer with a telephone handset in the on hook position is illustrated. With the telephone handset 10 in the on-hook position, sterilizer switch 16 is actuated. The on-hook signal to from the sterilizer switch 16 is sent to the timer/power circuit 18 which begins a present timing sequence and completes a circuit thereby providing power to UV lamps 22. As noted above, upon expiration of the preset time of the timing circuit 18, the UV lamps 22 are extinguished. Alternatively, if the telephone handset 10 is removed from the cradle of the telephone, the circuit is broken by the action of the sterilizer switch 16, thereby extinguishing the UV lamps.

Power to the telephone handset sterilizer is provided by external power 32, and or battery power 30.

Earpiece seal 28 and mouthpiece seal 29 provide both a visual and gaseous seal and engage the sides of the telephone handset mouthpiece and earpiece so that a user cannot see the UV illumination from the UV lamps 22 and so that the ozone gas produced by the UV lamps cannot escape. As can be seen in FIG. 2, when the telephone handset 10 is placed with the cradle, the earpiece fits snugly within the earpiece portion 24 of the cradle and the mouthpiece of the telephone handset 10 fits snugly within the mouthpiece portion 26 of the cradle.

Figure 3:
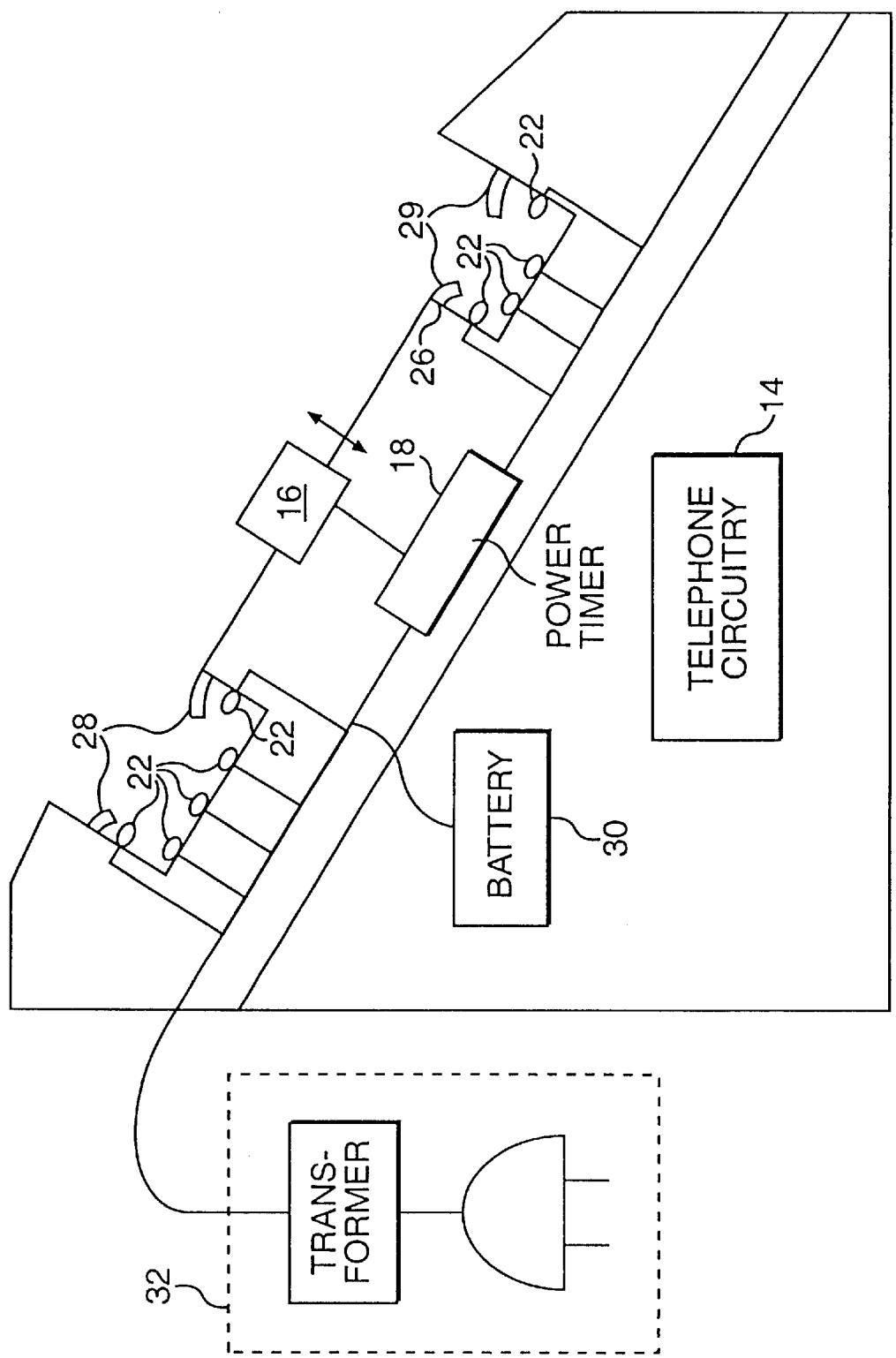
FIG. 3 illustrates the telephone handset sterilizer without handset.

Referring to FIG. 3 the telephone handset sterilizer without handset in the cradle is illustrated. In this situation, the sterilizer switch 16, which is spring loaded and biased in the "off" position breaks the circuitry to the timer/power circuit 18 and hence extinguished the UV lamps 22 halting both the UV illumination and the production of ozone. Seal 28 and 29 are shown but not in contact with the telephone handset earpiece and mouthpiece.

Figure 4:
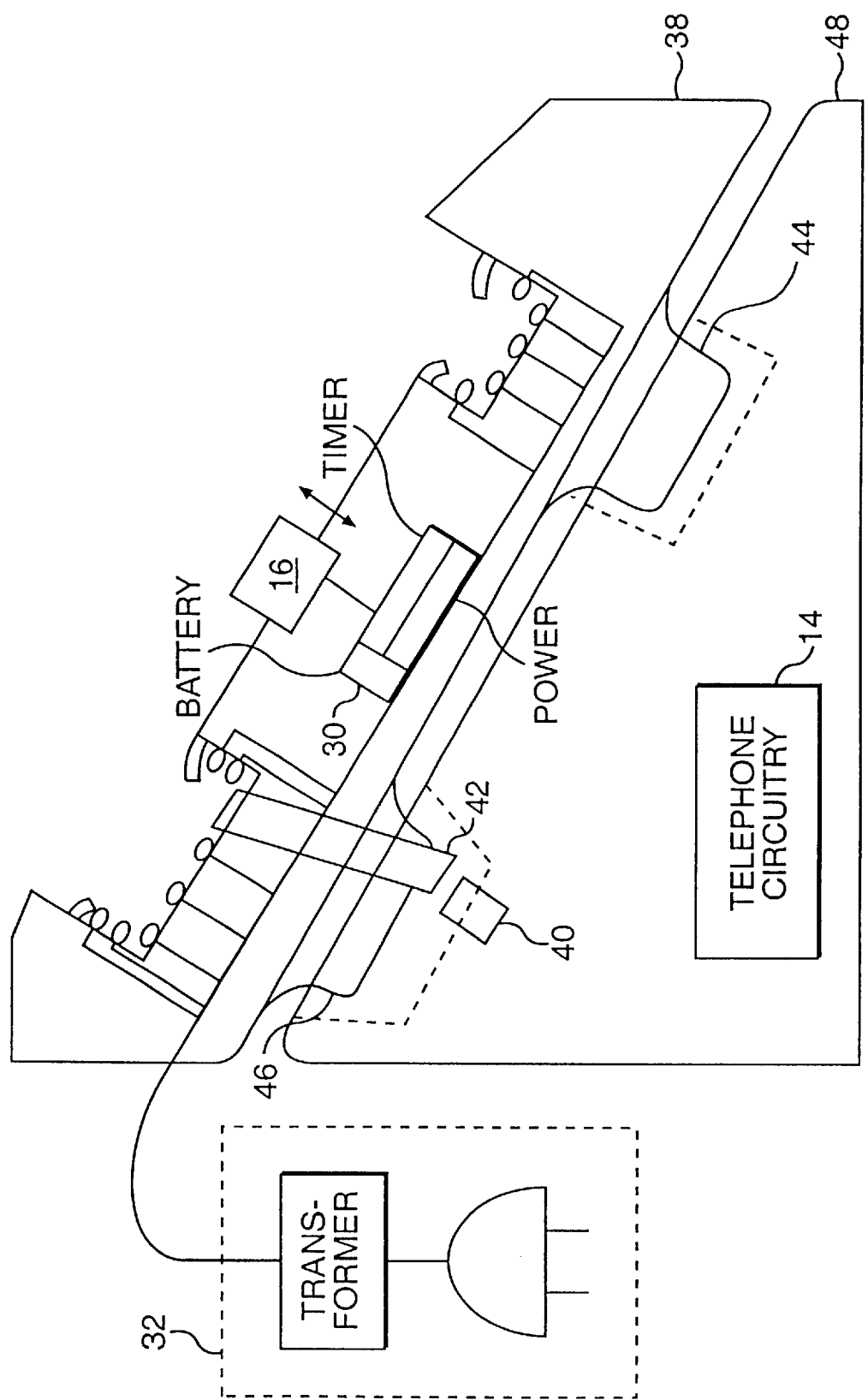
FIG. 4 illustrates a retrofit unit telephone handset sterilizer.

Referring to FIG. 4 a retrofit unit telephone handset sterilizer is illustrated. This unit is shown as a separate unit 38 that fits into the normal telephone cradle or cradle portion of an integrated telephone unit 48. The retrofit handset sterilizer 38 is secure to or fits into the normal cradle of the telephone. In the FIG. 4, the retrofit handset sterilizer engages the normal telephone cradle 48 by downward protrusions 44, 46 which fit into the normal housings for the telephone mouthpiece and earpiece although this is not meant as a limitation. For example, a hook-and-loop fastening means could be affixed to the telephone cradle and the retrofit sterilizer to keep the retrofit sterilizer in position. If the retrofit sterilizer is offered as an option, the telephone cradle could be manufactured with fasteners or fastener holes for a simple positive attachment of the retrofit sterilizer to the telephone cradle 48.

In the retrofit handset sterilizer, battery power 30 resides within the retrofit sterilizer and may be rechargeable batteries or single use batteries. Additionally, external household current 32 can be supplied.

Whether as an integrated unit, as shown in FIG. 2 and 3, or as a retrofit sterilizer as shown in FIG. 4, alternate embodiments are to provide power from household current, from rechargeable or single use batteries, or both.

Figure 5:
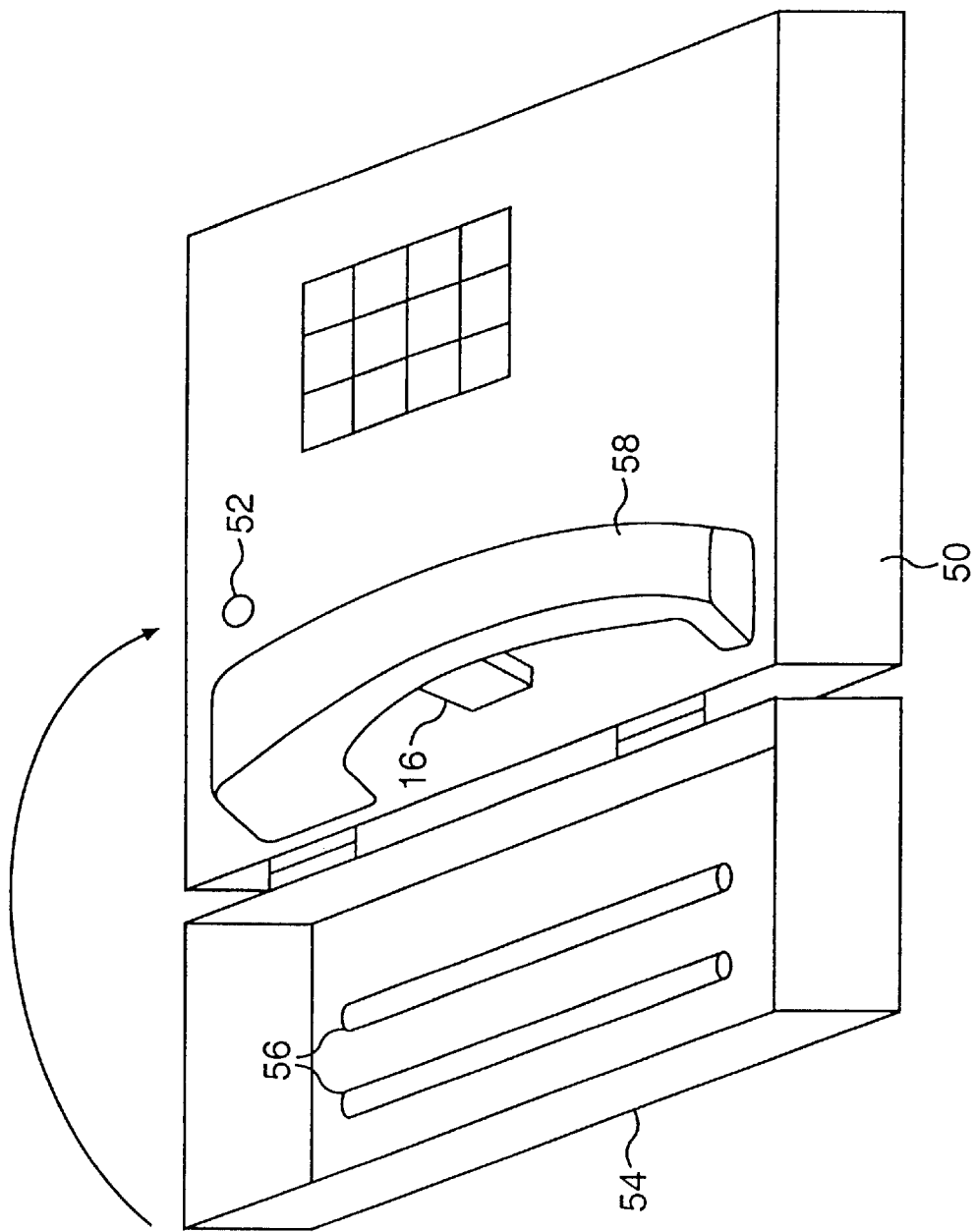
FIG. 5 illustrates the telephone handset sterilizer with a hinged handset cover.

Referring to FIG. 5 the telephone handset sterilizer with a hinged handset cover is illustrated. In this alternate embodiment, the telephone handset sterilizer described above is present, but not shown. However, a hingedly attached cover is present which swings over and covers the telephone handset 58. The telephone handset 58 is shown engaging sterilizer switch 16 which can actuate the sterilizer circuit and hence the sterilization already described. In addition, handset cover 54 may also comprise its own UV lamps that are energized when the cover engages a second sterilizer switch 52. When switch 52 is engaged by handset cover 54, handset cover UV lamps are turned on thereby sterilizing the handset from above and releasing small amounts of ozone to further sterilize the telephone handset. The duty cycle of the handset cover UV lamps is controlled by the same timer/power circuit 18 (not shown) described earlier.

It should be noted that the number of lamps depicted in the various figures is not meant to be limiting. For example in certain embodiments it may be more appropriate to have more than two lamps in the handset cover and fewer or greater numbers of lamps in the mouthpiece and earpiece housings of the handset cradle. Further while the lamps are shown as individual tube type lamps, alternative shapes are well within the state-of-the-art including U-shaped lamps, ring-shaped lamps individual bulb-type lamps, and indeed any other lamp that will emit the appropriate ultraviolet radiation necessary for the sterilization.

It should be noted that the position of indicator lights (not shown) is entirely arbitrary and can be placed anywhere on the apparatus to provide satisfactory convenient viewing by the user.

As noted earlier, ultraviolet radiation in the 200 nm range generates ozone gas. In sufficient quantities ozone gas can have a germicidal effect. Therefore apertures in the supporting means for the telephone handset are provided to allow circulation of the ozone gas so that additional germicidal effects in addition to those of the ultraviolet radiation may occur.

As noted earlier, the timer circuit period of time can be preset based upon the optimum time necessary to achieve sterilization. In the event that the telephone handset is not lifted within the time period established in the timer circuit 18 the UV sterilization lamps will go off after the passage of the optimum sterilization time. In event that handset is lifted before the time for sterilization has expired, the timer 18 is reset and the sterilization period begins again when the telephone handset is placed in the on-hook position. In this fashion power to UV sterilization lamps 22 is turned off after the appropriate sterilization period thereby saving lamp life and prolonging useful life of the ultraviolet sterilization lamps.

In the locations where UV sterilization lamps 22 are present, a quartz material or any other material that is transparent to ultraviolet radiation is used to support the telephone handset between the UV lamps 22 and the telephone handset.

A method and apparatus for sterilization of telephone handsets has been shown. Various alternative embodiments of the present invention have also been shown by reference to the figures contained herein. Common to all of these embodiments are the UV sterilization lamps, sterilization switch that is engaged when the telephone handset is in the on-hook position, and power and timing circuits to provide timed sterilization for telephone handsets which automatically turn the UV sterilization off when the preset timer time expires.

It will be appreciated by those skilled in the art that other embodiments may be possible employing the common elements of the present invention that have been described above without departing from the scope of the invention as disclosed.

What is claimed is:

1. A sterilizer for suppressing germs on a telephone handset having an earpiece and a mouthpiece, the sterilizer comprising:
   a telephone handset cradle;
   a telephone handset cover hingedly attached to the telephone cradle and positioned to cover the telephone handset when the telephone handset cover is closed over the telephone handset when the telephone handset is in the on-hook position;
   a sterilizer switch biased to an off position, positioned to engage the telephone handset cover when the telephone handset cover is closed over the telephone handset;
   a timed power circuit connected to the sterilizer switch for providing timed application of power;
   a first ultraviolet (UV) source mounted within the telephone handset cover and connected to the timed power circuit for receiving the timed application of power, the first UV source being positioned to illuminate the telephone handset when the telephone handset cover is closed over the telephone handset; and
   a power supply connected to the timed power circuit;
   wherein, when the sterilizer switch is switched to an on position upon engaging the telephone handset cover when the telephone handset cover is closed over the telephone handset, the timed power circuit is caused to provide the timed application of power to the first UV source, and wherein, when the telephone handset cover is not closed over the telephone handset, no power is supplied to the first UV source.

2. The telephone handset sterilizer of claim 1 wherein the first UV source emits ultraviolet radiation below 200 nm and creates ozone gas.

3. The telephone handset sterilizer of claim 1 wherein the the first UV source emits ultraviolet radiation above 200 nm.

4. The telephone handset sterilizer recited in claim 1, the sterilizer further comprising a second UV source disposed within the telephone handset cradle, wherein the second UV source is illuminated by the timed power circuit when the telephone handset cover is closed over the telephone handset.

5. The telephone handset sterilizer recited in claim 4, the sterilizer further comprising sterilizer seals positioned to engage the earpiece and the mouthpiece of the telephone handset when the telephone handset is in the on-hook position, for preventing UV radiation from the second UV source from escaping the telephone handset cradle.

6. The telephone handset sterilizer recited in claim 4, wherein the telephone handset cradle comprises an earpiece cradle and a mouthpiece cradle.

7. The telephone handset sterilizer of claim 1 wherein the power supply is a battery power supply.

8. The telephone handset sterilizer of claim 7 wherein the battery supply is taken from the group consisting of rechargeable batteries and single use batteries.

9. The telephone handset sterilizer of claim of claim 1 wherein the power supply is normal household current.

10. The telephone handset sterilizer of claim 1 wherein the timed application of power to the first UV source is of a duration sufficient to effect sterilization of the telephone handset.

11. The telephone handset sterilizer recited in claim 6, wherein the second UV source is positioned both in the earpiece cradle and in the mouthpiece cradle, and is further positioned to illuminate the handset earpiece and the handset mouthpiece.

12. The telephone handset sterilizer recited in claim 4, wherein the second UV source comprises at least one UV emitting lamp.

13. The telephone handset sterilizer recited in claim 6, wherein the second UV source comprises a plurality of UV lamps.

14. The telephone handset sterilizer of claim 13 wherein the plurality of UV lamps are positioned with the earpiece cradle and within the mouthpiece cradle.

15. The telephone handset sterilizer of claim 5 wherein the sterilizer seals comprise a flexible material taken from the group consisting of rubber, silicone, nylon, and latex.

16. A retrofit telephone handset sterilizer comprising:
   (a) a removable telephone hand set cradle adapted to be removably attached to a telephone handset cradle of a normal telephone;
   (b) a sterilizer switch biased to the "off" position, positioned to engage a telephone handset when the telephone handset is placed an on-hook position;
   (c) a timer/power circuit connected to the sterilizer switch for providing the timed application of power;
   (d) an ultraviolet (UV) source mounted within the telephone handset cradle and connected to the timer/power circuit for receiving the timed application of power, and positioned to illuminate the telephone handset having and earpiece and mouthpiece;
   (e) a power supply connected to the timer/power circuit; and
   (f) wherein when the sterilizer switch is engaged to the "on" position when the telephone handset is placed in the on-hook position thereby signaling the timer/power circuit to provided the timed application of power to the UV source, and wherein when the telephone hand set is in the off-hook position, no power is supplied to the UV source.

17. The retrofit telephone handset sterilizer of claim 16 wherein the ultraviolet source emits ultraviolet radiation below 200 nm and creates ozone gas.

18. The retrofit telephone handset sterilizer of claim 16 wherein the ultraviolet source emits ultraviolet radiation above 200 nm.

19. The retrofit telephone handset sterilizer of claim 16 further comprising sterilizer seals positioned to engage the earpiece and the mouthpiece of the telephone handset when the telephone handset is in the on-hook position, for preventing UV radiation from escaping the telephone handset cradle.

20. The retrofit telephone handset sterilizer of claim 16 wherein the telephone handset cradle comprises an earpiece cradle and a mouthpiece cradle.

21. The retrofit telephone handset sterilizer of claim 20 wherein the UV source is positioned in the earpiece cradle and in the mouthpiece cradle is further positioned to illuminate the handset earpiece and the handset mouthpiece.

22. The retrofit telephone handset sterilizer of claim 16 wherein the power supply is a battery power supply.

23. The retrofit telephone handset sterilizer of claim 22 wherein the battery supply is taken from the group consisting of rechargeable batteries and single use batteries.

24. The telephone handset sterilizer of claim of claim 16 wherein the power supply is normal household current.

25. The retrofit telephone handset sterilizer of claim 16 wherein the timed application of power to the UV source is of a duration sufficient to effect sterilization of the telephone handset.

26. The retrofit telephone handset sterilizer of claim 16 wherein the UV source comprises at least one UV emitting lamp from the group of UV wavelength ranges consisting of above 200 nm and below 200 nm.

27. The retrofit telephone handset sterilizer of claim 20 wherein the UV source comprises a plurality of UV lamps.

28. The retrofit telephone handset sterilizer of claim 27 wherein the plurality of UV lamps are positioned with the earpiece cradle and within the mouthpiece cradle.

29. The retrofit telephone handset sterilizer of claim 19 wherein the sterilizer seals comprise a flexible material taken from the group consisting of rubber, silicone, nylon, and latex.

30. A method for sterilizing a telephone handset, the telephone handset comprising an earpiece and a mouthpiece, the method comprising:
    actuating a sanitizing switch by closing a handset cover when the telephone handset is placed on hook;
    applying timed application of power to a UV light source disposed in the handset cover when the sanitizing switch is actuated; and
    illuminating the telephone handset with UV light from the UV light source.

31. The method for sterilizing the handset of a telephone of claim 30 wherein applying the timed application of power comprises applying power for a time sufficient to sterilize the telephone handset.

32. The method for sterilizing the handset of a telephone of claim 30 wherein the UV light source is from the UV wavelength group consisting of above 200 nm and below 200 nm.

33. The method for sterilizing the handset of a telephone of claim 30 further comprising additionally sterilizing the telephone handset with ozone gas when the UV light source is below 200 nm.

34. The method for sterilizing the handset of a telephone of claim 30 further comprising sealing the area around the telephone handset earpiece and mouthpiece to visually block the UV illumination from the UV light source.

35. The method for sterilizing the handset of a telephone of claim 30 wherein illuminating the telephone handset with UV light comprises illuminating the telephone handset earpiece in a telephone handset earpiece cradle and illuminating the telephone handset mouthpiece in a telephone handset mouthpiece cradle.

\* \* \* \* \*